United States Patent [19]
Dschida

[11] Patent Number: 5,854,056
[45] Date of Patent: Dec. 29, 1998

[54] FUNGAL CELL WALL PRODUCTION AND UTILIZATION AS A RAW RESOURCE FOR TEXTILES

[76] Inventor: William J. A. Dschida, 1807 Columbus Ave., McKinleyville, Calif. 95519

[21] Appl. No.: 980,441

[22] Filed: Nov. 28, 1997

[ * ] Notice: The term of this patent shall not extend beyond the expiration date of Pat. No. 5,

[51] Int. Cl.$^6$ ..................................... C12N 1/14
[52] U.S. Cl. .................... 435/254.1; 435/254.4; 435/256.8
[58] Field of Search ................ 435/242, 254.1, 435/254.11, 254.4, 256.8; 162/1, 55, 91

[56] References Cited

U.S. PATENT DOCUMENTS

| | | |
|---|---|---|
| 2,811,442 | 10/1957 | Van Horn et al. . |
| 3,616,246 | 10/1971 | Cherry . |
| 4,873,196 | 10/1989 | Selitrennikoff .......................... 435/254 |

FOREIGN PATENT DOCUMENTS

| | | | |
|---|---|---|---|
| 499153 | 1/1954 | Canada .................................. | 435/242 |
| 606897 | 8/1948 | United Kingdom .................... | 435/242 |

OTHER PUBLICATIONS

Johnson M.A.; "Mycelial Paper a Potential Resource Recovery Process"; Biotechnol Bioeng 20 (7). 1978 1063–1084.

Johnson et al., Biotechnology and Bioengineering, vol. 20: pp. 1063–1084, 1978.

Muzzarelli, Chapter 6, Industrial Production and Application, pp. 207–213, in Chitin, Pergamon Press, Oxford, England, 1977.

Domszy et al., Chapter 42, pp. 463–473, in Cellulose and Its Derivatives, J.F. Kennedy, ed., Horwood, Chichester, UK, 1985.

*Primary Examiner*—David A. Redding
*Attorney, Agent, or Firm*—Bell, Boyd & Lloyd

[57] ABSTRACT

The present invention reveals a product from fungi and a method for making the product. The method involves producing spores from a filamentous fungus, producing mycelia from the spores, growing the mycelia into a flat sheet, and recovering the fungus product. The fungus product is used as a raw resource for the production of textiles.

19 Claims, 4 Drawing Sheets

Fig. 2

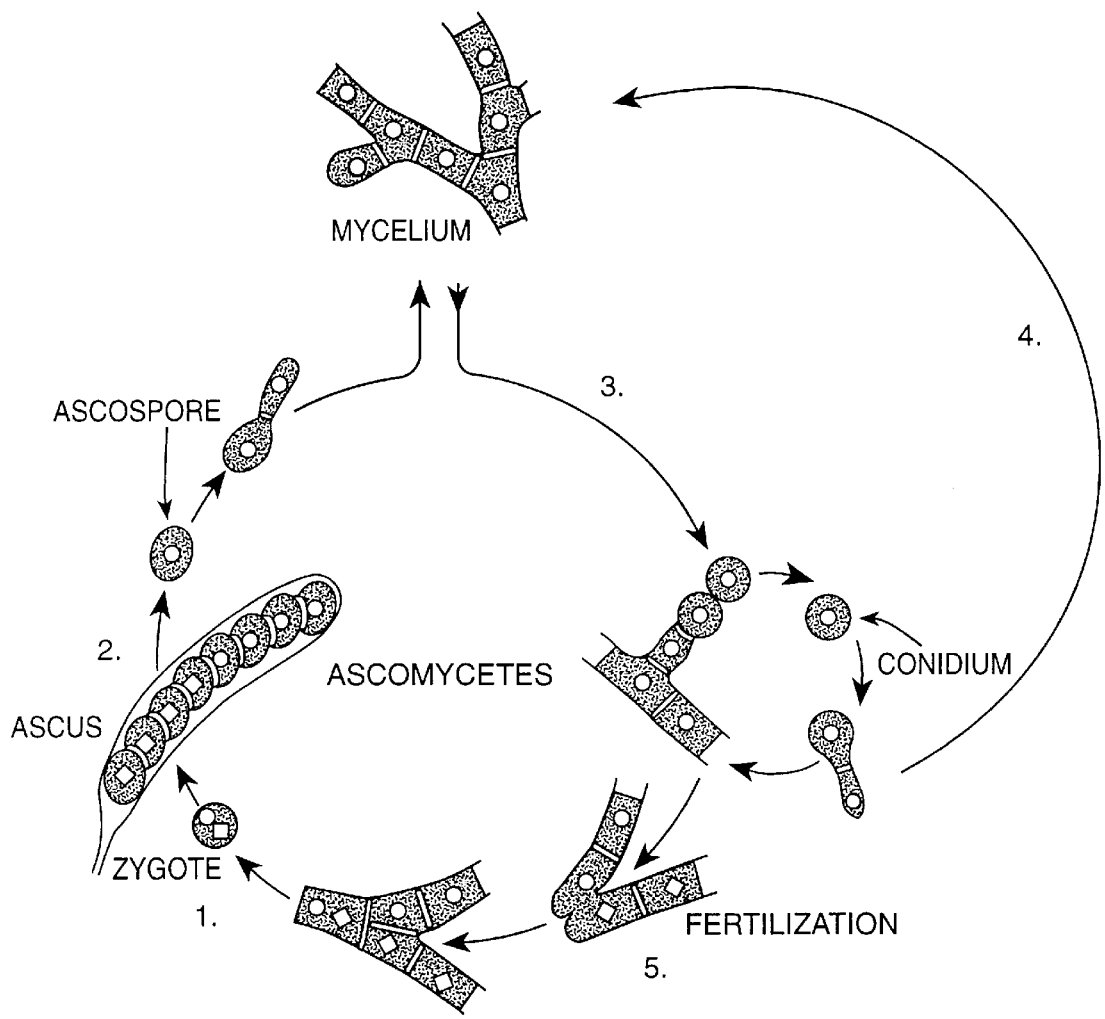

1. THE FUNGAL ZYGOTE, THE ONLY DIPLOID NUCLEUS OF THE FUNGAL LIFE CYCLE, IS FORMED IN SPECIALIZED STRUCTURES KNOWN AS THE ASCUS IN ASCOMYCETES.
2. MEIOSIS OCCURS AND SEXUAL SPORES ARE PRODUCED AND RELEASED.
3. THE SPORES GERMINATE AND, IN FILAMENTOUS FUNGI, DEVELOP INTO LONG HYPHAE WHICH TERMINATE WITH BUDDING STRUCTURES PRODUCING ASEXUAL SPORES.
4. ASEXUAL SPORES CAN PERPETUATE THE FILAMENTOUS STAGE OF THE FUNGUS.
5. HYPHAE OF OPPOSITE MATING TYPES INTERACT AND FUSION OCCURS WHICH PRODUCES THE SEXUAL STRUCTURE CONTAINING, FOR EXAMPLE, THE ZYGOTE PRODUCING ASCI.

5,854,056

FUNGAL CELL WALL PRODUCTION AND UTILIZATION AS A RAW RESOURCE FOR TEXTILES

This patent application is directly related to U.S. Provisional patent application Ser. No. 60/065,280, filed Nov. 10, 1997.

BACKGROUND OF THE INVENTION

1. Field of the Invention

The present invention describes a method for the culturing of filamentous fungi specifically for the production of cell wall components, where the components can be used as a raw resource for the production of textiles. The novel method uses solid and liquid media in culturing the microorganisms to a desired degree in their hyphae-producing stage of their life-cycle. The fungi are cultured under aerobic and nutrient-rich conditions at standard temperature and pressure. By maximizing the vegetative phase of the fungal growth cycle, cell wall material can be produced in abundance at a logarithmic rate that rivals the production of any modern, cellulose-based pulp industry.

More specifically, the method described herein involves the production of spores from filamentous fungi; the production of mycelia from the spores; growth of the mycelia into flat sheets; and recovery of a fungal product or fungal pulp. The fungal product is used as a raw resource for the production of a variety of textiles and textile products.

2. Description of the Related Art

The cellulose industry—that which supplies the demand for paper, cardboard, clothing, fabrics, lumber, construction materials, etc.—is the world's largest textile producer. The demand for cell wall or pulp, the raw textile exploited to fulfill this need, is met mostly through the harvesting and processing of plant fiber, especially timber. Unfortunately, some of the logging, industrial, and chemical practices used to procure and process this resource are destructive—especially to local environments harboring this industry. Although interest in other plant fibers, e.g., flax, sisal, hemp, has been renewed as supplemental sources for timber-cellulose, the need for alternative methods of cell wall production is greater now than ever before.

The fastest growing organisms, aside from unicellular bacteria, are fungi, especially the filamentous types. Some fungi are capable of doubling their mass in liquid culture every 1.5–2 hours. Fungi are similar to plants in many ways. Fungi produce cell wall components, the most abundant of which are cellulose and a modified version of the same called chitin. Most of the fungal body matter is comprised of cell wall, either that which is presently being synthesized and laid down or that which has been constructed and left behind. Of the cell wall components, 25% can be composed strictly of the β-type glucans, the most abundant oligosaccharides of these being cellulose and chitin (ref. 1).

Given the simple growth requirements of vegetative, filamentous fungi, that is, water, nutrients, oxygen, and warmth, fungal pulp can be cultured for much less than the overall money invested into wood pulp production. Moreover, the environment would greatly benefit from this new technology, e.g., by the elimination of pulp pollution sources. Eventually, fungal pulp could replace wood pulp, thereby diminishing the demand for timber. Yet, this simple cost analysis still does not reflect the huge savings in time alone when growing or producing fungal pulp versus timber for wood pulp.

Fungi have evolved to utilize nearly any substrate as a food source with which to build their elaborate, tubular bodies and networks, made principally of cellulose- and chitin-based microfibril components, for the purpose of succeeding against nearly every adverse condition. This very adaptation is what plagues organic and living matter, as well as plastic, toxic, and dead or dying matter, and has made the war against fungi one of the most difficult and costly wars humans have ever waged against another organism. We ought to utilize fungi's superior capability to produce its own cell wall with all of its own natural qualities, especially its high strength and resiliency to microbial attack, and use this as a basic component to meet the demands of human needs, e.g., food, clothing, and textiles.

Numerous patents and scientific procedures exist for which hyphae of filamentous fungi are used in spore production and organelle isolation (refs. 2–9). For example, U.S. Pat. No. 3,616,246 (Cherry) discloses a process for the production of fungal spores. In the process, mycelia are spread in a thin layer upon an absorptive surface, incubated, and spores produced and recovered. U.S. Pat. No. 4,873,196 (Selitrennikoff) discloses conditional protoplasts of temperature-sensitive variants of the osmotic-1 mutant strain of *Neurospora crassa* and methods for making the protoplasts. Both Canadian Patent 499,153 (Moyer) and British Patent 606,897 (Moyer) disclose an improved method for the production of mold spores.

In this patent, we describe a method for growing filamentous fungi from any of the divisions of the phylum Fungi. For example, in the lower fungi are the saprophytic oomycetes, the "water molds" or "cellulosic fungi" because of the characteristic lack of chitin in their cell wall. In the higher fungi are the divisions of the zygomycetes, e.g., the "bread molds" and most endo-mycorrhizal fungi; the ascomycetes, e.g., the "sac fungi" or common molds; the deuteromycetes, e.g., the asexual fungi; and the basidiomycetes, e.g., the "club/mushroom fungi" and most ecto-mycorrhizal fungi. All of these examples of fungi possess a filamentous stage in their life-cycles that exploits the fungi's uncanny ability to extend itself out into the environment, efficiently utilizing local resources to produce more of itself, namely, hyphal tubes and reproductive structures, both sexual and asexual. Thus, it is an object of the present invention to describe a method for the culturing of filamentous fungi specifically for the production of cell wall components, where the components can be used as a raw resource for the production of textiles.

SUMMARY OF THE INVENTION

The present invention discloses a product, fungal pulp, from fungi and a method for making the fungal pulp. The method, as outlined in FIG. 1, is comprised of the following steps:

a) producing spores from a filamentous fungus,
b) producing mycelia from the spores,
c) growing the mycelia into a flat sheet, and
d) recovering the fungal pulp.

In the first step, spores are produced in an aqueous medium or on a solid medium by inoculating the medium with spores from a filamentous fungus, germinating and growing the fungal hyphae on the medium until spore formation ceases.

In the next step, mycelia are produced from the spores by inoculating aqueous nutrient broth with the spores, and growing the filamentous mycelia in the aqueous nutrient broth aerobically.

In the following step, mycelia are grown into a flat sheet by placing the mycelia into a shallow trough containing replenished nutrient broth and allowing the hyphal filaments from adjacent mycelia to intermesh.

In the final step, fungal pulp is recovered by draining the nutrient broth from the shallow trough or culture, washing the intermeshed mycelia, and drying the intermeshed mycelia.

The method may be performed with a filamentous fungus selected from the group consisting of ascomycetes, basidiomycetes, deuteromycetes, oomycetes, and zygomycetes. The method is preferably performed with a filamentous fungus selected from the group consisting of Neurospora, Pisolithus, Poria, and Saprolegnia. The method is more preferably performed with a filamentous fungus selected from the group consisting of *Neurospora crassa, Pisolithus tinctorius, Poria olaracea*, and *Saprolegnia ferax*. The method is most preferably performed with *Neurospora crassa* as the filamentous fungus.

The present invention also discloses the fungal pulp produced from the method for making the fungal pulp. This fungal pulp can be used as a raw resource for the production of textiles and related materials.

BRIEF DESCRIPTION OF THE DRAWINGS

FIG. 2 shows a schematic representation of the life cycle of *Neurospora crassa*, a filamentous fungus.

DETAILED DESCRIPTION OF THE PREFERRED EMBODIMENT

Figure 1:
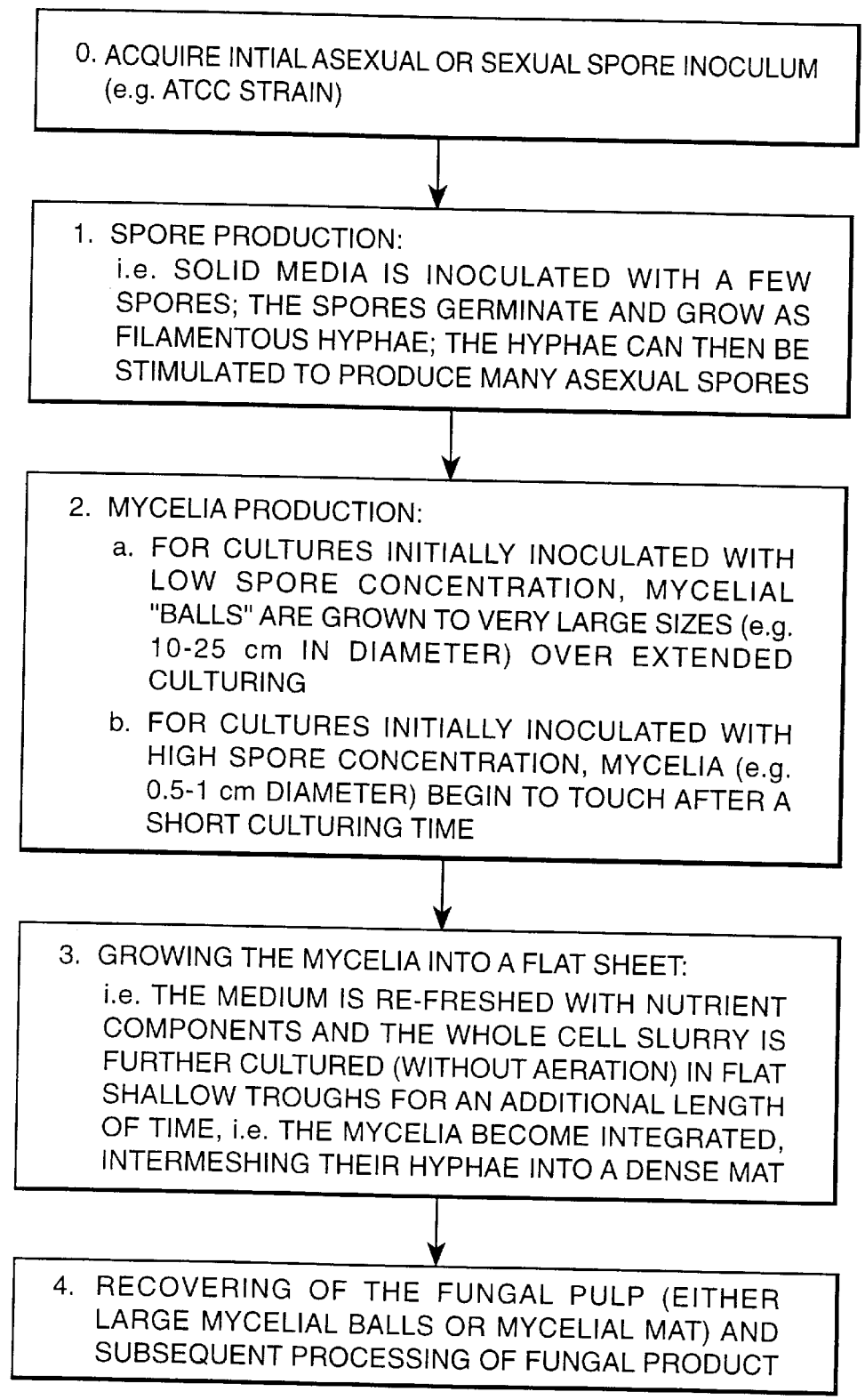
FIG. 1 shows a simplified flow chart of the method of the present invention, that is, a general outline for a method for the production of fungal pulp.

The present invention uses the vegetative (haploid) growth cycle of filamentous fungi for the production of extracellular matrix, that is, the material secreted outside of the cell to make the cell wall. Isolation of the fungal mass and the subsequent treatment(s) to the cell wall matrix processes the raw material into a product with a wide variety of applications, especially as a new resource for the world's textile industry.

More specifically, the cell wall products include the microfibrillar exoskeleton or the outer shell of the fungi's thread-like vegetative hyphal cells, as opposed to the sexual, "mushroom" or fruiting body of the fungi.

FIG. 2 shows a schematic representation of the life cycle of *Neurospora crassa*, a filamentous fungus. The fungal zygote, the only diploid nucleus of the fungal life cycle, is formed in specialized structures known as the ascus in ascomycetes. Meiosis occurs and sexual spores are produced and released. The spores germinate and, in filamentous fungi, develop into long hyphae which terminate with budding structures producing asexual spores.

Asexual spores can perpetuate the filamentous stage of the fungus; hyphae of opposite mating types interact and fusion occurs which produces the sexual structure containing, for example, the zygote producing asci. Other examples of filamentous fungi include ascomycetes, basidiomycetes, deuteromycetes, oomycetes, and zygomycetes.

In this Description, the following definitions are specifically used:

Fungal mass: a term used to describe the conglomerate of fungus in the medium at any given point in production.

Spore: the haploid, asexual bud or sexual reproducing unit "seed" of a fungus. An example of an asexual bud is a conidiospore or micro-/macro-conidium; pl., –conidia. Examples of a sexual reproducing unit "seed" include an ascospore and a basidiospore.

Hypha (Pl., hyphae): the thread-like, cellular tube of filamentous fungi which emerge and grow from the germinating fungal spore.

Microfibril: the long stacks of cellulose/chitin-rich filaments which constitute the long, linear polysaccharide chains of the cell wall matrix and ultimately the main component of plant pulp and other cellulose-based textiles.

Mycelium (Pl., mycelia): the collection of hyphal tubes originating from a single spore and branching out into the environment (radially on solid media; spherically in liquid media).

Primary pulp: the fungal cell slurry which is comprised of the non-integrated mycelia.

Secondary Pulp: the fungal mat which is comprised of the integrated mycelia.

FUNGAL CULTURING FOR CELL WALL PRODUCTION

Methodology

Procedures for culturing filamentous fungi for pulp production

Sterile conditions are maintained throughout the procedure to control for contamination by bacteria, insects or other fungi.

1. Producing spores from a filamentous fungus

The first step of the present invention conceptually resembles other spore production procedures that employ filamentous fungi cultured on solid and liquid media for spore production (refs. 2–9). "Scaling-up" the spore inoculum is usually the critical, first step to increase the final harvest of a particular fungal metabolite or product. In other words, larger numbers of spores in the beginning translates into larger numbers of harvestable yield (products or metabolites) in the end.

Solid nutrient medium is comprised mainly of water, a simple sugar/carbohydrate source, vitamins/macro-/micro-nutrients, and agar. The medium is prepared, put into containers with large surface area, sterilized, and cooled. The sterile nutrient solution is inoculated with spores, usually of the asexual form, e.g., conidiospores, of a desired filamentous fungus. An extensive list of filamentous fungal strains that could be used in the present invention is disclosed in the Filamentous Fungi publication available through the American Type Culture Collection, ATCC (ref. 11).

The fungal spores are germinated and grown under conditions which produce large amounts of fungal spores. These spores are subsequently used for inoculating large volumes of sterile, liquid media for mycelial cell wall production.

In general, culture vessels are filled with defined, sterilized, and cooled medium. The sterile medium can then be inoculated with a "stab" or "loopful" of a spore suspension. Cultures are incubated for vegetative, hyphal growth and stimulated for spore production. Flasks with mature spores can be used directly or stored for later use.

EXAMPLE 1

Production of spores of the ascomycete fungus, *Neurospora crassa*

The ascomycete *Neurospora crassa* (ATCC accession number 9279; ref. 11, 12) was cultured in a chemically-defined medium (Vogel's: ATCC medium 331; ref. 11) under defined conditions (refs. 6–7). The sterile, solid medium was inoculated with a "stab" or "loopful" of a conidiospore suspension of *Neurospora crassa*. Cultures were incubated for 5 days at 30° C. in the dark for vegetative, hyphal growth followed by 5 days at 25° C. in the light to stimulate spore production. Flasks with spores were stored for short-term (one to two weeks) at 4° C. or long-term (months) at −20°/−80° C.

For sexual spores of this species, hyphae from the opposite mating types must come into contact, fuse, and undergo syngamy and meiotic divisions, as well as the concomitant cellular divisions and sexual spore production. Ascospores were heat-shocked at 60° C. to stimulate germination.

EXAMPLE 2
Production of spores of the basidiomycete fungus, *Pisolithus tinctorius*

The basidiomycete Pisolithus tinctorius was cultured with simple potato-dextrose medium (ATCC media 336: ref. 11). Spores were obtained from the ATCC (strain accession number 46384: ref. 11). The mycelia grew at 24°–30° C. for up to several weeks until spores were completely formed.

EXAMPLE 3
Production of spores of the basidiomycete fungus, *Poria olaracea*

For spore production in the basidiomycete, Poria olaracea, pure culture was obtained from the ATCC (accession number 18410: ref. 11). A yeast-malt liquid media (ATCC medium 200: ref. 11) was inoculated and the mycelia grew optimally at 30° C. for 7–14 days. Within a month, waxy patches developed on the surface mycelia, producing basidia, i.e., sexual spore-producing structures. The basidiospores were collected and subsequently used to inoculate liquid or agar-media cultures. Since this inoculum is a product of sexual recombination, it has higher genetic variability and is therefore not as homogenous as inoculum of the asexual spores (ref. 11, 15).

EXAMPLE 4
Production of spores of the oomycete fungus, *Saprolegnia ferax*

The water molds are common and easily cultured. The oomycete *Saprolegnia ferax* was cultured using a cornmeal agar media (ATCC medium 307: ref. 11, 16). Liquid cultures were inoculated with the spores from the ATCC (accession number 42593: ref.11) and incubated at 20°–24° C. until mycelial growth had stopped (approximately two to four days).

Since *Saprolegnia ferax* is a water mold, an aqueous medium was necessary for spore-production. Yet, as soon as the hyphae were exposed to an increase in oxygen concentration, spore production commenced. After spores matured they were collected and either used directly as inoculum or stored for later use.

Due to the cost of making defined medium, less expensive components, i.e., with more basic and simple ingredients, and other culturing factors are being tested to maximize asexual spore production. Examples of the less expensive medium components and other culturing factors currently under investigation are as follows:

1. different vitamin and mineral sources, e.g., peptone or brewer's yeast;
2. different carbohydrate sources, e.g., corn, potato, rice, barley, and at varying concentrations;
3. sterile aeration directly into spore flasks or plates or $O_2$-gas injection for increased spore production;
4. different lighting conditions to stimulate spore production; and
5. different culturing containers, e.g. into larger expensive vessels in order to increase surface area for aeration.

These investigations into the less expensive medium components and other culturing factors are for optimization of the present methods and are not intended to limit the scope of the present method as herein described and claimed.

2. Producing mycelia from the spores

In general, sterilized liquid medium is comprised mostly of water, complex carbohydrates, simple sugars, vitamins, and macro- and micro-nutrients. The medium is inoculated with conidial spores, typically in the range of $10^{6-12}$ conidia/liter liquid medium. The fungi are then grown filamentously in warm, aerated liquid cultures to either the primary or secondary pulp stages. Depending on the filamentous fungal type used as well as the culturing conditions under which it will be grown, e.g., temperature and nutrient concentrations; vessel size and shape; and initial inoculum concentrations, the culturing methodology could vary widely.

The microscopic attributes of the fungus directly affect the final product's characteristics, e.g., texture, flexibility, strength, color, etc. A number of culturing factors or specific feature(s) of a particular fungal strain, i.e., those which affect the anatomy and physiology of the fungus in culture, are responsible for the characteristics of the final pulp product. For example:

1. Different initial spore concentrations or initial inoculum densities may be used to affect final fungal product characteristics.
2. Different temperatures, concentrations of sugar and nutrients, or rates of aeration may be used to affect the rate of fungal growth.
3. Different filamentous fungal mutants may be used to produce different amounts of hyphal branching.
4. Different filamentous fungal mutants may be used to affect the timing of hyphal branching.
5. Different filamentous fungal strains or mutants may be used to affect the thickness of hyphae.
6. Different filamentous fungal mutants may be used to affect the length of hyphae.
7. Different filamentous fungal mutants may be used to affect the amount of particular cell wall constituents, e.g., cellulose:chitin.
8. Different filamentous fungal mutants or culturing times may be used to affect the degree of integration among individual mycelial clumps.
9. Different color mutants of filamentous fungi may be used to produce different shades or colors of fungal pulp.

These examples of culturing factors and specific feature (s) of a particular fungal strain are for optimization of the present methods and are not intended to limit the scope of the present method as herein described and claimed.

3. Growing the mycelia into a flat sheet

In general, mycelia were grown into a flat sheet by placing the mycelia into a shallow trough containing nutrient broth and allowing the mycelia to grow until filaments from adjacent mycelia intermesh. Hyphal intermeshing is the process into which the mycelia are forced. This produces a product equal to an interwoven mat of chitinous-cellulosic strands, thus capitalizing on all the benefits of fungal cell wall through massive overgrowth under super-optimized conditions.

A. Mycelial production to the primary pulp stage

The acetone method (ref. 7) is used to determine the dry weight of mycelia/liter of media, especially regarding the dry weight of a given strain at optimal culture density. The optimal culture density is defined as that density at which the mycelia occupy the majority of the liquid medium. For example, mycelia occupy 75–100% of the total volume of the liquid medium. The culture has reached optimal density when the hyphal tips of the individual mycelia begin to touch and intermesh, i.e., hyphae begin to grow into adjacent mycelia. The primary pulp culture is ready for harvesting when the dry weight is 1–5 gm of mycelia/liter.

This initial fungal product is referred to as the primary or loose fungal pulp. The fungal mass is ready for harvesting when the mycelial units are occupying the majority of space within the liquid medium and hyphal tips of neighboring fungal spheres are touching. If the mycelia are allowed to grow into large, individual hyphal spheres, e.g., 10–25 cm in diameter, a product similar to construction "chip-board" could be produced.

Figure 3:
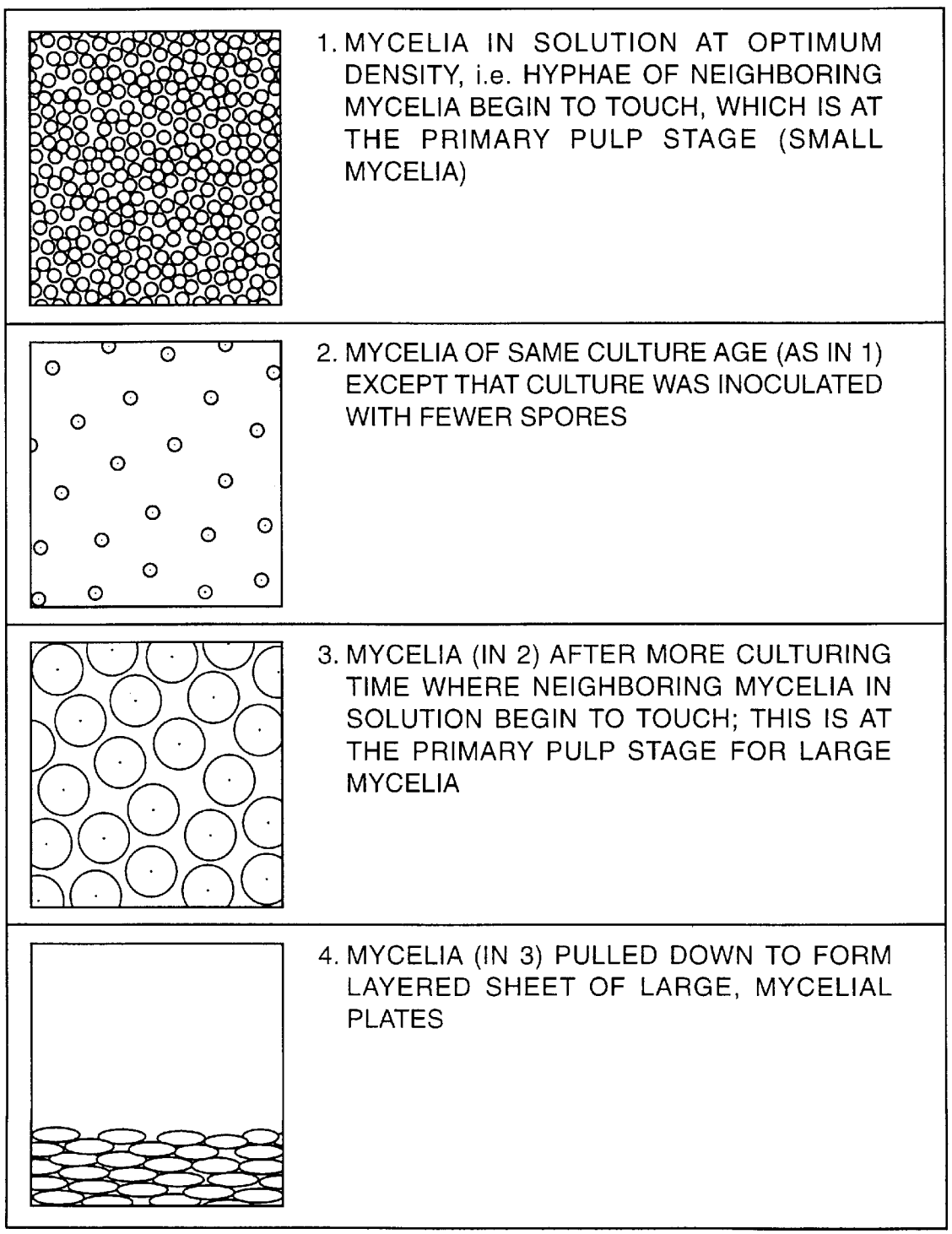
FIG. 3 shows the culturing of mycelia for primary pulp production.

FIG. 3 shows the culturing of mycelia for primary pulp production. Mycelia are depicted in solution at optimum density, i.e. hyphae of neighboring mycelia begin to touch, which is at the primary pulp stage (small mycelia). Mycelia of same culture age are also depicted except that this culture was inoculated with fewer spores. These mycelia after more culturing time demonstrate how neighboring mycelia in solution begin to touch; this is at the primary pulp stage for large mycelia. The mycelia are then pulled down to form layered sheet of large, mycelial plates

EXAMPLE 5

Production of *N. crassa* mycelia to the primary pulp stage

A 10-liter carboy was filled with Vogel's minimal medium (refs. 6–9). The liquid cultures were inoculated at a spore concentration of $10^9$ conidia/liter of medium. The cultures were well aerated with a bubbler/aeration-tube at a rate of 1–10 liters of air/minute per liter of medium and maintained at 25°–30° C. for 12–16 hours.

EXAMPLE 6

Production of *P. tinctorius* mycelia to the primary pulp stage

A potato-dextrose liquid media (ATCC medium 336: ref. 11) was inoculated with sexual spores at a final concentration of $10^9$ spores/liter and cultured aseptically with a high rate of aeration at 24°–30° C. The culture was grown for one to four days until the cultured mycelia began to intermesh.

EXAMPLE 7

Production of *P. olaracea* mycelia to the primary pulp stage

A yeast-malt liquid media (ATCC medium 200: ref. 11) was inoculated with sexual spores at a final concentration of $10^9$ spores/liter and cultured aseptically with a high rate of aeration at 24°–30° C. until the cultured mycelia began to intermesh.

EXAMPLE 8

Production of *S. ferax* mycelia to the primary pulp stage

As an oomycete, this fungus is adapted to an aqueous environment with low oxygen. Therefore, in order to stimulate mycelial production, liquid cultures were left stationary instead of being shaken or aerated. Cornmeal liquid media (ATCC medium 307: ref. 11, 16) was inoculated with spores at $10^9$ spores/ml and incubated at 24°–30° C. for up to 14 days.

Due to the cost of defined media, less expensive ways to culture filamentous fungi are being assessed to maximize mycelia production. Examples of less expensive ways that are being investigated are as follows:

1. different vitamin and mineral sources; and
2. different carbohydrate sources and concentrations.

B. Mycelial production to the secondary pulp stage

The fungal cell slurry is further cultured. The cultures need to be supplemented with fresh nutrient solution to stimulate vegetative growth of the peripheral hyphal tips into adjacent mycelia. The action of cross-weaving neighboring fungal units allows the fungal mass to integrate itself together into one large, continuous net of dense matting.

Growth of the cultures continues in warm, liquid medium until the desired level of integration is produced. The final density and degree of adjacent-cell overlap is determined ultimately by the final thickness and age of the culture. At this point, the fungus in culture is such a dense slurry of homogeneous mycelia that the threat of foreign, fungal or bacterial contamination is greatly diminished. Therefore, sterility beyond this point in the process should be less of a problem.

Figure 4:
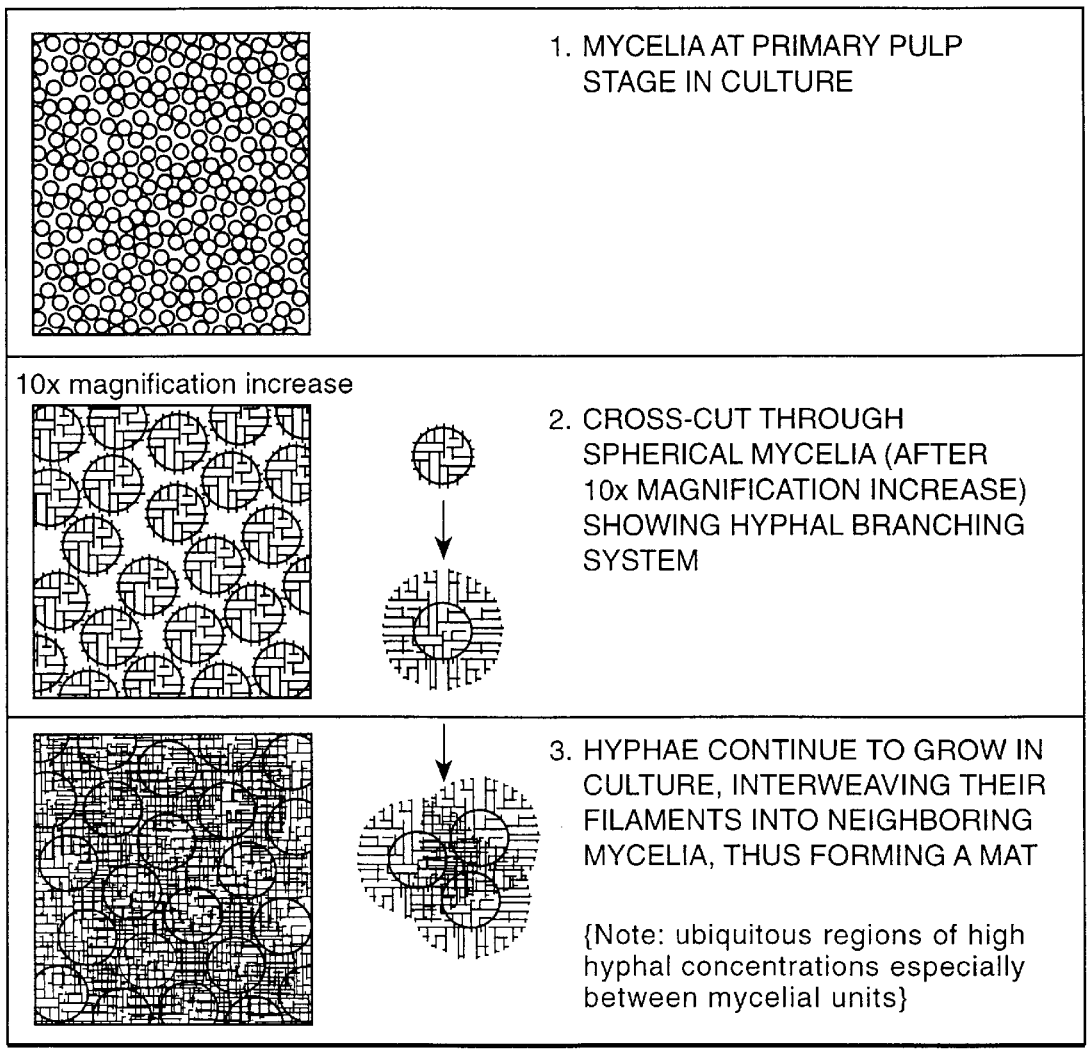
FIG. 4 shows the culturing of mycelia for secondary pulp production or matting.

In order to insure adequate oxygenation of the respiring culture, i.e., consuming sugars and $O_2$ and exhausting $CO_2$, the fungal mycelia in the stationary liquid medium require large surface-aeration fans or some other means of increasing fresh air circulation over the surface of the cultures. This requirement is critical to maximize gas exchange between the carbon dioxide-rich culture medium and the ambient oxygen-rich air. The degree of overlap between neighboring fungal units can be monitored with a microscope as well as controlled by culturing conditions. Once the mycelia have reached the desired level of integration, the product is referred to as the secondary pulp or mat. FIG. 4 shows the culturing of mycelia for secondary pulp production or matting. Mycelia are depicted at the primary pulp stage in culture and at 10× magnification in cross-section to demonstrate hyphal branching system. When hyphae are allowed to continue to grow in a replenished culture medium, their filaments interweave with those of the neighboring mycelia, thus forming a dense mat of intertwined hyphae. The bottom of the figure depicts the ubiquitous regions of high hyphal concentrations especially between mycelial units.

EXAMPLE 9

Production of *N. crassa* mycelia to the secondary pulp stage

Vogel's liquid media (ref. 6–9) was inoculated with spores at a final concentration of $10^9$ spores/liter and cultured aseptically with a high rate of aeration at 24°–30° C. until the cultured mycelia began to intermesh. The culture was transferred to a shallow trough for mycelial integration. Nutrient components were added to the fungal medium, e.g., 10% total medium volume of a 20× medium concentrate, to boost the nutrient content of the medium and further stimulate growth of the fungal mycelia into adjacent mycelia. The mycelial culture was then transferred to shallow troughs, i.e. fungal broth was approximately 1–2 centimeter (0.5–1 inch) deep to allow for adequate gas ($O_2$ and $CO_2$) exchange. The mycelia were grown at 25°–30° C. for approximately 8–16 hours within which time the hyphal tips of adjacent mycelial units continued to grow and integrate or inter-weave their hyphae. The dry weight of the final fungal pulp approached 5–10+ mg/ml for a dense mat of secondary pulp.

EXAMPLE 10

Production of *P. tinctorius* mycelia to the secondary pulp stage

Yeast-malt liquid media (ATCC medium 336: ref. 11) was inoculated with spores at a final concentration of $10^9$ spores/liter and cultured aseptically with a high rate of aeration at 24°–30° C. until the cultured mycelia began to intermesh.

The culture was transferred to a shallow trough for mycelial integration. The broth was enriched with fresh nutrients and the hyphal mat allowed to grow and interweave neighboring hyphae at 24°–30° C. for up to 14 days until the mycelia formed a dense mat.

EXAMPLE 11
Production of *P. olaracea* mycelia to the secondary pulp stage

A malt-dextrose liquid media (ATCC medium 200: ref. 11) was inoculated with spores at a final concentration of $10^9$ spores/liter and cultured aseptically with a high rate of aeration at 24°–30° C. until the cultured mycelia began to intermesh. The culture was transferred to a shallow trough for mycelial integration. The broth was enriched with fresh nutrients and the hyphal mat allowed to grow and inter-weave neighboring hyphae at 24°–30° C. for up to 14 days.

EXAMPLE 12
Production of *S. ferax* mycelia the secondary pulp stage

The liquid cultures were left stationary instead of being shaken or aerated. Liquid cornmeal media (ATCC medium 307: ref. 11) was inoculated with spores at $10^9$ spores/ml and incubated at 24°–30° C. for up to 14 days or until neighboring mycelia began to integrate.

Culturing techniques are being assessed to optimize production of mycelia, e.g., switching from 10-liter carboys to 1,000–1,000,000 liter industrial mixers. Investigation into 1,000,000-liter bio-reactors, e.g. vessels used in commercial fungal culturing for antibiotics, wine, and beer production, suggests that this level of high-volume production is a near-future reality.

These investigations into the less expensive medium components and other culturing factors are for optimization of the present methods and are not intended to limit the scope of the present method as herein described and claimed.

4. Recovering the fungal pulp

The final product, either primary or secondary pulp, is then drained and/or strained of its bathing or nutrient solution, washed, rinsed, and dried. The processing steps are specific to the type of fungus and textile desired, i.e., cell wall characteristics dictate the treatments necessary and specific wash treatments serve to remove specific components or create modifications to the cell wall material. Ionic washes and/or organic solvent can be incorporated to create desired effects.

After a final water wash, the product is dried to approximately 90% of its original wet weight. The fungal pulp can then be used as a resource for a variety of textile applications depending on desired characteristics of the final product.

After removing medium from culture, the resultant fungal mat is thoroughly washed with distilled water at least two times. The whole mycelial-cell product may be rinsed and dried at this point or further processed to remove certain fungal components, e.g., lipid membranes or to modify specific cell wall constituents. The following list demonstrates a few subsequent steps that could follow the initial water rinses:

1. ionic wash for ionic-displacement of metabolite from cell wall matrix, i.e., to remove charged, attached metabolites, e.g., the acetylamine group on chitin;
2. detergent wash to remove organic components, e.g., lipids and organelles;
3. final water rinses to remove the previous wash solutions.

These examples of subsequent steps are for optimization of the present methods and are not intended to limit the scope of the present method as herein described and claimed.

EXAMPLE 13
Processing of *N. crassa* for the fungal product

Once the final fungal product has integrated in a dense mat, the resultant pulp was removed from the nutrient medium by straining the fungal mass out from the solution on a rigid screen and releasing the bathing solutions through sieves at the bottom of the troughs. The fungal mat was rinsed twice with distilled water to remove any remaining medium using spray nozzles to uniformly rinse and wash the subtending pulp. The fungal mat was then air dried on a screen in a 45° C. oven overnight. This process constitutes the simplest embodiment of the processing of a fungal product.

Alternatively, for more extensive processing, the rinsed mat was washed with an ionic detergent solution of 0.1% sodium dodecyl sulfate and rinsed twice with distilled water. In order to ionically wash the cell wall of weakly-bound ionic components, the mat was washed with a saline solution of 100 mM KCl followed again with several distilled water washes to remove the last remaining wash solutions. Treatment to de-acetylate the chitin into chitosan was accomplished using a dilute alkaline solution (ref. 18). The fungal product was then washed several times with distilled water. Finally, the processed fungal pulp was dried either by warm room air or in a heated oven (45°–60° C. overnight), cut into sheets, and layered for storage.

The processing of the mycelial product for the other fungi was essentially identical to the process described for Neurospora. The chitin content relative to the cellulose content of the cell wall preparation may require different chemical processing, e.g. varied amounts of de-acetylation or de-amination. In the case of Saprolegnia, chitin is absent in the cell walls. In general, the final processing of fungal cell wall pulp for all of the filamentous fungal divisions was as detailed above.

In a conveyor-type industrial facility, the mycelial product could progress through a series of washing, rinsing, and drying steps in order to efficiently process the raw fungal material. For example, a screen track could move the fungal pulp/mat under spray-jets to rinse and wash the product, dry the washed mat over heating units, and ultimately cut and stack the final product for finish-processing and export.

As human history has dictated interest to particular fungal strains, usually to stop the spread of disease, so also have their virtues been revealed to the wary audience. For example, a diverse assortment of dyes and colors have been extracted from the pigments in fungi and lichenous actinomycetes for centuries. A rainbow of molds are found on agricultural plants: the oomycete Peronospora, the blue mold of tobacco; the deuteromycetes Thielaviopsis, the black rot of tobacco; and Botrytis, the gray mold of fruit. Colored fungi are found also on forest tree roots: the ecto-mycorrhizal basidiomycetes *Poria sequoiae*, the creamy-yellow hyphae on decaying Redwood; and *Thelophora tellestris*, the brown hyphae on Spruce.

There also lies a large diversity of hyphal widths and morphologies: the actinomycete Streptomyces with submicron hyphal diameter; and the water mold Saprolegnia with hyphal diameters of over a millimeter (ref. 17). These differences in hyphal widths warrant deeper investigations into cell wall architecture, hyphal tube length and width, and their subsequent importance and utilization in textile production.

Additionally, the wall constituents of the fungal cell wall can vary as widely as the fungal divisions. For example, the lack of chitin in the walls of the oomycetes versus the array of chitin-derivatives found in the zygomycetes. As well, a wide diversity of polysaccharides can be found throughout the phylum; each with its own potential application in the textile industries.

Research by the present inventor has demonstrated that fungal mycelial products could be produced of various colors and textures, depending on the fungal strain and growth factors and/or conditions used in the process. From cultures of Neurospora started with a high spore inoculum and grown under optimized conditions, a final mycelial product analogous to a thick, felt-like mat was formed. The dried "parchment" was fairly rigid but strong enough not to break. The pulp product easily adhered to other surfaces as well as cohering to other moistened layers of the same product forming a plywood-like product. Thinner preparations of the same mat were more flexible, like plastic wrap. Even in its unrefined stage, the sheet had remarkable resiliency and tensile strength. Again, these simple observations reveal a textile resource with great potential for a wide variety of applications.

The following is a list of some of the important benefits of the invention described, i.e., production of a new, cellulose-based pulp product.

1. Little or no chemical treatment is required for the production of raw, processed product. For example, white fungal paper can be produced using albino mutant strains. There is no need for chemical bleaching of the pulp. In contrast, numerous chemicals are used in the processing in the wood pulp or paper manufacturing industries. Additionally, lignin is the main contaminant in wood pulp and must be removed. There is no lignin in fungal hyphae.
2. A variety of natural colors can be produced in the fungal product without chemical treatment. For example, albino white, cream, yellow, orange, peach, pink, gray, and brown can be created in the fungal product by using an appropriate mutant strain of filamentous fungi.
3. Different fungal strains and mutants can be used or mixed for different and desired qualities in the final product.
4. Fungal pulp can also be mixed with "rag" or plant fibers, e.g., cotton, flax, hemp, wood, as done in the wood-paper industry for a variety of texture effects.
5. Fungal byproducts from the procedure are rich in organic material and can be used in other industrial applications.
6. Fungal product or fungal pulp can be produced in geographical regions that lack the natural resources such as trees yet possess an inexpensive carbohydrate source for growing fungal cultures.
7. Savings in time and money can be achieved by producing fungal pulp via simple culturing techniques.

Potential Markets for Fungal "Pulp" Resource

The following is a partial list of textiles markets where the fungal pulp could be utilized:

1. paper and other paper products;
2. food wrapping;
3. clothing material;
4. building and construction material, e.g., fiberboard;
5. absorbent material, e.g., disposable diapers;
6. medical applications, e.g., anti-microbial wound dressings;
7. adhesive coating, i.e., mucopolysaccharides and charged polypeptides in cell wall stick to a wide variety of surfaces;
8. food product, e.g., fungal cakes.

The main force behind this new technology is the filamentous fungi's powerful, driving potential to grow at a logarithmic rate. The fungal population can double its entire mass every few hours during the logarithmic, vegetative phase of their life cycle and continue to perpetuate this phenomenal rate of growth indefinitely given optimized, local environmental conditions, as described above. Take for example a vat—equal in size to the volume of a healthy, 200 year-old Redwood tree (height, 75 m or 250 ft.; average shoulder width, 2 m or 6 ft.). If this "Redwood vat" were filled with liquid-nutrient media and inoculated with *Neurospora crassa* conidiospores at an initial concentration and under conditions described below, fungal hyphae could be cultured, processed and a fungal cell wall product could be produced within 30 days (ten, 2.5 day cultures managed successively in the "Redwood vat"). The amount of the cell wall produced would be equal in mass to that of the Redwood tree which took 200 years to produce. Another major advantage for this future industry is that the fungi could be cultured and harvested, and the fungal product processed and dried into raw pulp in the same facility, allowing for more centrally located and managed fungal textile plants.

The importance of this fungal-textile technology concept cannot be overstated. The beauty of it lies in this technology's simplicity; low cost; ease and speed of production of a raw, usable product; low impact to the environment, i.e., no bleaching or chemical processing, thus little pollution; centralized operation and efficiency of operation; and its extreme adaptability to a broad spectrum of food sources for the cell wall-producing fungi in culture, e.g., corn, potato, rice, wheat/oat/barley or other grains, as well as organic industrial waste.

This new technology can be implemented nearly anywhere, especially in third world nations and in countries lacking vegetation for pulp production where some forms of carbohydrate source are available. Given the tremendous demand for plant resources, especially soft wood conifers, to supply the cellulose-based textile industry, filamentous fungi appear to be a sound alternative to our present and future world dilemma.

References

The following is a list of the patents and scientific articles cited throughout this application. All patents and articles cited herein are hereby incorporated by reference in their entirety and relied upon.

1. Burnett, J. H., Aspects of the Structure and Growth of Hyphal Walls, in *Fungal Walls and Hyphal Growth*, eds. J. H. Burnett and A. P. J. Trinci, Cambridge University Press, Cambridge, pp. 1–25, 1990.
2. Cherry, E., U.S. Pat. No. 3,616,246, Use of Absorptive Materials for the Production of Fungus Spores, 1971.
3. Selitrennikoff, C. P., U.S. Pat. No. 4,873,196, Protoplasts of Temperature-sensitive Strains of *Neurospora crassa* os-1, 1989.
4. Moyer, A. J., Canadian Patent Number 499,153, Methods for Producing Mold Spores and Inoculation of Culture Media, 1954.
5. Moyer, A. J., U.S. Pat. No. 606,897, Improvements in or Relating to a Method of Inoculating a Liquid Culture Medium with Mould Spores, 1948.
6. Vogel, H. J., *American Naturalist* 98:435, 1964.
7. Davis, R. H. and F. J. deSerres, Genetic and Microbiological Research Techniques for *Neurospora crassa*, *Methods in Enzymology* 17A:79–143, 1970.
8. Bowman, E. J. and B. J. Bowman, Purification of Vacuolar Membranes, Mitochondria, and Plasma Membranes from *Neurospora crassa* and Modes of Discriminating Among the Different H+-ATPases, *Methods in Enzymology* 157:562–73, 1988.
9. Dschida, W. J., Structure and Regulation of Vacuolar ATPase from *Neurospora crassa*, Ph.D. Dissertation, University of California at Santa Cruz, 1994.
10. Bartnicki-Garcia, S., Cell Wall Chemistry, Morphogenesis, and Taxonomy of Fungi, *Annual Review of Microbiology* 22:87–108, 1968
11. ATCC (American Type Culture Collection) Filamentous Fungi, publ., American Type Culture Collection, Rockville, Md., 19th Edition, 1996.
12. Catalogue of Strains: Fungal Genetic Stock Center Catalog, Supplement to *Fungal Genetic Newsletter*, No. 43 (Kansas City, Kans.), 6th Edition, 1996.
13. Stamens, P. and J. S. Chilton, The Mushroom Cultivator: A Practical Guide to Growing Mushrooms at Home, 1995.
14. Marx, D. H. and D. S. Kenney, Production of Ectomycchorrhizal Fungus Inoculum, in *Methods and Principles of Mycorrhizal Research*, ed. N. C. Schenk, The American Phytopathological Society, St. Paul, 1982.
15. Davidson, R. W., F. F. Lombard, and R. R. Hirt, Fungi Causing Decay in Wooden Boats, *Mycologia* 39:313–327, 1947.
16. Gleason, F. H., Nutritional comparisons in the Leptomitales, *American Journal of Botany* 55:1003–1010, 1968.
17. Malloch, D., *Moulds: their Isolation, Cultivation, and Identification*, University of Toronto Press, Toronto, 1981.
18. Foster, A. B., and J. M. Webber, in *Advances in Carbohydrate Chemistry* (M. L. Wolfrom and R. S. Tipson, eds.), Vol. 15, pp. 371–393. Academic Press, New York.

While the invention has been described in connection with what is presently considered to be the most practical and preferred embodiments, it is to be understood that the invention is not limited to the disclosed embodiments, but on the contrary is intended to cover various modifications and equivalent arrangements included within the spirit and scope of the appended claims.

Thus, it is to be understood that variations in the present invention can be made without departing from the novel aspects of this invention as defined in the claims.

What is claimed is:

1. A method for producing fungal pulp, comprising the steps of:
   a) producing spores from a filamentous fungus;
   b) producing mycelia from the spores;
   c) growing the mycelia into a flat sheet,
   wherein the mycelia are grown into a flat sheet by:
      i) placing the mycelia into a shallow trough containing nutrient broth and
      ii) allowing the mycelia to grow until filaments from adjacent mycelia intermesh; and
   d) recovering the fungal pulp.

2. The method of claim 1, wherein the spores are produced on a solid medium by:
   i) inoculating aqueous agar medium with asexual conidial spores,
   ii) allowing the aqueous agar medium to solidify into a solid medium, and
   iii) germinating and growing the spores on the solid medium in the dark.

3. The method of claim 2, wherein the mycelia are produced from spores by:
   i) inoculating an aqueous nutrient broth with spores and
   ii) growing the mycelia in the aqueous nutrient broth aerobically.

4. The method of claim 1, wherein the spores are produced in an aqueous medium by:
   i) inoculating the aqueous medium with asexual conidial spores, and
   ii) germinating and growing the spores in the aqueous medium in the dark.

5. The method of claim 1, wherein the fungal pulp is recovered by:
   i) draining the nutrient broth from the shallow trough,
   ii) washing the intermeshed mycelia, and
   iii) drying the intermeshed mycelia.

6. The method of claim 1, wherein the filamentous fungus is selected from the group consisting of ascomycetes, basidiomycetes, deuteromycetes, oomycetes, and zygomycetes.

7. The method of claim 1, wherein the filamentous fungus is selected from the group consisting of Neurospora, Pisolithus, Poria, and Saprolegnia.

8. The method of claim 7, wherein the filamentous fungus is selected from the group consisting of *Neurospora crassa, Pisolithus tinctorius, Poria olaracea*, and *Saprolegnia ferax*.

9. The method of claim 8, wherein the filamentous fungus is *Neurospora crassa*.

10. A fungal pulp produced by the steps of:
    a) producing spores from a filamentous fungus;
    b) producing mycelia from the spores;
    c) growing the mycelia into a flat sheet,
    wherein the mycelia are grown into a flat sheet by:
       i) placing the mycelia into a shallow trough containing nutrient broth and
       ii) allowing the mycelia to grow until filaments from adjacent mycelia intermesh; and
    d) recovering the fungal pulp.

11. The fungal pulp of claim 10, wherein the spores are produced on a solid medium by:
    i) inoculating aqueous agar medium with asexual conidial spores,
    ii) allowing the aqueous agar medium to solidify into a solid medium, and
    iii) germinating and growing the spores on the solid medium in the dark.

12. The fungal pulp of claim 10, wherein the spores are produced in a liquid medium by:
    i) inoculating aqueous medium with asexual conidial spores, and
    ii) germinating and growing the spores in the aqueous medium in the dark.

13. The fungal pulp of claim 11, wherein the mycelia are produced from spores by:
    i) inoculating an aqueous nutrient broth with spores and
    ii) growing the mycelia in the aqueous nutrient broth aerobically.

14. The fungal pulp of claim 10, wherein the fungal pulp is recovered by:
    i) draining the nutrient broth from the shallow trough,
    ii) washing the intermeshed mycelia, and
    iii) drying the intermeshed mycelia.

15. The fungal pulp of claim 10, wherein the filamentous fungus is selected from the group consisting of ascomycetes, basidiomycetes, deuteromycetes, oomycetes, and zygomycetes.

16. The fungal pulp of claim 15, wherein the filamentous fungus is selected from the group consisting of Neurospora, Pisolithus, Poria, and Saprolegnia.

17. The fungal pulp of claim 16, wherein the filamentous fungus is selected from the group consisting of *Neurospora crassa, Pisolithus tinctorius, Poria olaracea*, and *Saprolegnia ferax.*

18. The fungal pulp of claim 17, wherein the filamentous fungus is *Neurospora crassa.*

19. A method for producing fungal pulp, comprising the steps of:

a) producing spores from a filamentous fungus;

b) producing mycelia from the spores;

c) growing the mycelia into a flat sheet, wherein the mycelia are grown into a flat sheet by:
   i) placing the mycelia into a shallow trough containing nutrient broth and
   ii) allowing the mycelia to grow until filaments from adjacent mycelia intermesh; and d) recovering the fungal pulp, wherein the fungal pulp is recovered by:
   i) draining the nutrient broth from the shallow trough,
   ii) washing the intermeshed mycelia,
   iii) drying the intermeshed mycelia and
   iv) recovering the fungal pulp as an interwoven mat.

* * * * *